US010405988B2

(12) United States Patent
Grotz et al.

(10) Patent No.: US 10,405,988 B2
(45) Date of Patent: *Sep. 10, 2019

(54) SPINAL IMPLANT WITH EXPANDABLE FIXATION

(71) Applicant: Howmedica Osteonics Corp., Mahwah, NJ (US)

(72) Inventors: R. Thomas Grotz, Las Vegas, NV (US); Rudy A. Pretti, Auburn, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/938,442

(22) Filed: Mar. 28, 2018

(65) Prior Publication Data

US 2018/0333270 A1    Nov. 22, 2018

Related U.S. Application Data

(63) Continuation of application No. 14/594,569, filed on Jan. 12, 2015, now Pat. No. 9,931,222, which is a
(Continued)

(51) Int. Cl.
*A61F 2/44* (2006.01)
*A61F 2/46* (2006.01)
(Continued)

(52) U.S. Cl.
CPC ............ *A61F 2/442* (2013.01); *A61F 2/4455* (2013.01); *A61F 2/4611* (2013.01);
(Continued)

(58) Field of Classification Search
CPC .......... A61F 2/44; A61F 2/4405; A61F 2/441; A61F 2/442; A61F 2/4455
See application file for complete search history.

(56) References Cited

U.S. PATENT DOCUMENTS 3,875,595 A    4/1975  Froning
4,932,975 A    6/1990  Main et al.
(Continued)

FOREIGN PATENT DOCUMENTS

DE    3729600 A1    3/1989
EP    1442715 A3    11/2004
(Continued)

OTHER PUBLICATIONS

Extended European Search Report for Application No. 11787340.6 dated Jun. 25, 2014.
(Continued)

*Primary Examiner* — Si Ming Ku
(74) *Attorney, Agent, or Firm* — Lerner, David, Littenberg, Krumholz & Mentlik, LLP

(57) ABSTRACT

A spinal implant which is configured to be deployed between adjacent vertebral bodies. The implant has at least one fixation element with a retracted configuration to facilitate deployment of the implant and an extended configuration so as to engage a surface of an adjacent vertebral body and secure the implant between two vertebral bodies. Preferably, the implant is expandable and has a minimal dimension in its unexpanded state that is smaller than the dimensions of the neuroforamen through which it must pass to be deployed within the intervertebral space. Once within the space between vertebral bodies, the implant can be expanded so as to engage the endplates of the adjacent vertebrae to effectively distract the anterior disc space, stabilize the motion segments and eliminate pathologic spine motion. Angular deformities can be corrected, and natural curvatures restored and maintained.

13 Claims, 6 Drawing Sheets

Related U.S. Application Data continuation of application No. 12/072,044, filed on Feb. 22, 2008, now Pat. No. 8,932,355.

(51) Int. Cl.
- A61F 2/28 (2006.01)
- A61F 2/30 (2006.01)
- A61F 2/48 (2006.01)

(52) U.S. Cl.
CPC .......... A61F 2002/2835 (2013.01); A61F 2002/3055 (2013.01); A61F 2002/30378 (2013.01); A61F 2002/30505 (2013.01); A61F 2002/30538 (2013.01); A61F 2002/30556 (2013.01); A61F 2002/30579 (2013.01); A61F 2002/30583 (2013.01); A61F 2002/30601 (2013.01); A61F 2002/30841 (2013.01); A61F 2002/4666 (2013.01); A61F 2002/4693 (2013.01); A61F 2002/485 (2013.01); A61F 2210/0085 (2013.01); A61F 2220/0025 (2013.01); A61F 2220/0033 (2013.01); A61F 2250/0006 (2013.01); A61F 2250/0009 (2013.01); A61F 2310/00023 (2013.01)

(56) References Cited

U.S. PATENT DOCUMENTS

| | | |
|---|---|---|
| 4,969,888 A | 11/1990 | Scholten et al. |
| 5,236,460 A * | 8/1993 | Barber .............. A61F 2/441 403/109.7 |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Butterman |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 * | 9/2002 | Cohen .............. A61F 2/4455 623/17.15 |
| 6,527,803 B1 | 3/2003 | Crozet et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,137,401 B2 | 3/2012 | Stad et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,574,297 B2 | 11/2013 | Stad et al. |
| 8,696,751 B2 | 4/2014 | Ashley et al. |
| 8,894,710 B2 | 11/2014 | Simpson et al. |
| 8,900,305 B2 | 12/2014 | Stad et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,545,316 B2 | 1/2017 | Ashley et al. |
| 9,814,600 B2 | 11/2017 | Shulock et al. |
| 2001/0056302 A1 | 12/2001 | Boyer et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2004/0030346 A1 | 2/2004 | Frey et al. |
| 2004/0088054 A1 | 5/2004 | Berry |
| 2004/0097928 A1 | 5/2004 | Zdeblick et al. |

(56) References Cited

U.S. PATENT DOCUMENTS

| | | |
|---|---|---|
| 2004/0133273 A1 | 7/2004 | Cox |
| 2004/0153065 A1 | 8/2004 | Lim |
| 2004/0186576 A1 | 9/2004 | Biscup et al. |
| 2005/0033437 A1 | 2/2005 | Bao et al. |
| 2005/0043800 A1 | 2/2005 | Paul et al. |
| 2005/0049590 A1* | 3/2005 | Alleyne ............... A61F 2/442 623/17.11 |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0256576 A1 | 11/2005 | Moskowitz et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0142861 A1* | 6/2006 | Murray ............... A61F 2/442 623/17.13 |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1* | 10/2007 | Grotz ............... A61F 2/442 623/17.11 |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0183204 A1 | 7/2008 | Greenhalgh et al. |
| 2008/0215153 A1 | 9/2008 | Butterman et al. |
| 2008/0243251 A1 | 10/2008 | Stad et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2010/0286783 A1 | 11/2010 | Lechmann et al. |
| 2011/0130835 A1 | 6/2011 | Ashley et al. |
| 2011/0137416 A1 | 6/2011 | Myers |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0245695 A1 | 9/2012 | Simpson et al. |
| 2012/0283830 A1 | 11/2012 | Myers |
| 2013/0096677 A1 | 4/2013 | Myers et al. |
| 2013/0158669 A1 | 6/2013 | Sungarian et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204374 A1 | 8/2013 | Milella, Jr. |
| 2013/0253650 A1 | 9/2013 | Ashley et al. |
| 2014/0018922 A1 | 1/2014 | Marino et al. |
| 2014/0031938 A1 | 1/2014 | Lechmann et al. |
| 2015/0148908 A1 | 5/2015 | Marino et al. |
| 2017/0224506 A1 | 8/2017 | Ashley et al. |
| 2018/0064557 A1 | 3/2018 | Shulock et al. |
| 2018/0098860 A1 | 4/2018 | To et al. |
| 2018/0116811 A1 | 5/2018 | Bernard et al. |
| 2018/0125671 A1 | 5/2018 | Bernard et al. |

FOREIGN PATENT DOCUMENTS

| | | |
|---|---|---|
| EP | 1415624 B1 | 5/2006 |
| JP | 2001-518824 A | 10/2001 |
| JP | 2008-502372 A | 1/2008 |
| WO | 2003003951 A1 | 1/2003 |
| WO | 2004016250 A1 | 2/2004 |
| WO | 2004016205 A3 | 5/2004 |
| WO | 2006044786 A3 | 1/2007 |
| WO | 2008011371 A3 | 3/2008 |
| WO | 2007124078 A3 | 7/2008 |
| WO | 2008039811 A3 | 7/2008 |
| WO | 2008112607 A3 | 12/2008 |
| WO | 2008148210 A1 | 12/2008 |
| WO | 2009033100 A1 | 3/2009 |
| WO | 2008121251 A3 | 8/2009 |
| WO | 2009064787 A3 | 8/2009 |
| WO | 2009105182 A1 | 8/2009 |
| WO | 2009114381 A1 | 9/2009 |
| WO | 2008086276 A3 | 12/2009 |
| WO | 2010068725 A3 | 10/2010 |
| WO | 2011011609 A3 | 6/2011 |
| WO | 2011150077 A1 | 12/2011 |

OTHER PUBLICATIONS

Extended European Search Report for Application No. EP14159619 dated Jun. 12, 2014.

International Search Report and Written Opinion dated Jun. 5, 2009 for related PCT/US2009/000974.

International Search Report and Written Opinion dated Apr. 10, 2008 in related International Application No. PCT/US2007/079474.

International Search Report and Written Opinion dated Aug. 13, 2010, in related International Application No. PCT/US2009/067446 filed Dec. 10, 2009.

International Search Report and Written Opinion dated Jun. 30, 2009, in related International Application No. PCT/US2008/003776 filed Mar. 21, 2008.

(56) References Cited

OTHER PUBLICATIONS

International Search Report and Written Opinion dated May 6, 2009, in related International Application No. PCT/US2009/000974 filed Feb. 17, 2009.
International Search Report and Written Opinion dated Nov. 11, 2010, in International Application No. PCT/US2010/031247 entitled "Insertion Handle for Implant."
International Search Report and Written Opinion dated Sep. 22, 2011 in related International Application No. PCT/US2011/037929.
State Intellectual Property Office of The People's Republic of China Search Report for Chinese Application No. 201510859939.8 dated Oct. 24, 2017.

* cited by examiner

SPINAL IMPLANT WITH EXPANDABLE FIXATION

CROSS-REFERENCE TO RELATED APPLICATIONS

This application is a continuation of U.S. patent application Ser. No. 14/594,569, filed on Jan. 12, 2015, which is a continuation of U.S. patent application Ser. No. 12/072,044, filed on Feb. 22, 2008, the disclosures of which are incorporated herein by reference.

FIELD OF THE INVENTION

The invention relates to devices and methods for stabilizing the vertebral motion segment. More specifically, the field of the invention relates to an expandable spinal implant with fixation elements to fix the implant within an intervertebral space while providing controlled spinal correction in three dimensions for improved spinal intervertebral body distraction and fusion.

BACKGROUND OF THE INVENTION

A conventional spine cage or implant is characterized by a kidney bean shaped body which is typically inserted in tandem posteriorly through the neuroforamen of the distracted spine after a trial implant creates a pathway. Existing devices for interbody stabilization have important and significant limitations, including inability to expand and distract the endplates while fixing the device to prevent relative movement between the device and an adjacent vertebral body. Current devices for interbody stabilization include static spacers composed of titanium, PEEK, and high performance thermoplastic polymer produced by VICTREX, (Victrex USA Inc, 3A Caledon Court; Greenville, S.C. 29615), carbon fiber, or resorbable polymers. Moreover, current interbody spacers do not maintain interbody lordosis and can contribute to the formation of a straight or even kyphotic segment and the clinical problem of "flatback syndrome." Separation of vertebral endplates increases space available for the neural elements, specifically the neural foramen. Existing static cages do not reliably improve space for the neural elements. Therefore, what is needed is a spinal implant that will provide space for the neural elements posteriorly between the vertebral bodies, or at least maintain the natural bone contours to avoid neuropraxia (nerve stretch) or encroachment.

Conventional devices for intervertebral body stabilization includes poor interface between bone and the biomaterial of the device. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings on the implant offer little resistance to movement applied to either side the endplates. Thus, nonunion is common in allograft, titanium and polymer spacers, due to motion between the implant and host bone.

BRIEF SUMMARY OF THE INVENTION

This invention is generally directed to a spinal implant for insertion between superior and inferior vertebral end plates after partial or total removal of a spinal disc. The spinal implant embodying features of the invention is easily installed and is capable of holding the vertebral or joint sections with increased pullout strength to minimize the chance of implant fixation loss during the period when the implant is becoming incorporated into the arthrodesis bone block.

More specifically, the invention is particularly directed to a spinal implant which has one or more extendable fixation elements that engage or penetrate vertebral end plates and prevent movement between the implant and the vertebral end plates after implantation. The one or more expandable fixation elements have a contracted configuration within the implant so as to not interfere with the insertion of the implant between vertebral bodies and have an extended configuration with a distal tip extending beyond the surface of the implant to engage the vertebral end plates after implantation and fix the position of the implant with respect to the adjacent vertebral body. The fixation element may be extended in a variety of ways such as with fluid pressure, e.g. hydraulic fluid, by mechanical force, such as a threaded connection with a rotating driving member or other suitable means. Fluidic displacement is preferred. The distal tip of the fixation element should be sharp enough to penetrate into the vertebral end plate.

Preferably, the spinal implant embodying features of the invention is an expandable spinal implant such as the selectively expanding spine cage described in copending application Ser. No. 11/535,432, filed on Sep. 26, 2006 and Ser. No. 11/692,800, filed on Mar. 28, 2007, which provides restoration of disc height between adjacent vertebrae and can provide corrective spinal alignment in a plurality of dimensions. Preferably, the implant has an interior cavity for receiving osteoconductive material to promote the formation of new bone in the intervertebral space subsequent to implanting.

A spinal implant having features of the invention has a base including a first pressure applying member such as an end plate with a first bone engaging surface, at least one extendable member cooperating with the base and a second upper pressure applying member with a second bone engaging surface coupled to the at least one extendable member. The one or more extendable fixation elements are configured to extend through passageways provided in the second upper pressure applying member and beyond the bone engaging surface thereof to penetrate into the adjacent vertebral end plate and fix the implant with respect to the vertebral body. Preferably, the fixation elements are slidably disposed within recesses within the extendable members.

The selectively expanding spine cage (SEC) or spinal implant embodying features of the invention is particularly suitable for posterior insertion between superior and inferior vertebral end plates as described in the aforementioned copending application Ser. Nos. 11/535,432 and 11/692,800. The SEC has an unexpanded configuration which allows easy deployment and is typically about 0.8 to about 1 cm in maximum short transverse dimension so as to enable minimal invasive insertion posteriorly between vertebral pedicles through a working space of approximately 1 cm in diameter. The extended fixation element extends beyond the tissue engaging surface of the second pressure applying member by at least 0.1 cm, preferably at least 0.25 cm to ensure proper engagement or contact with the end plate of the vertebral body and preferably penetration thereof.

In one preferred embodiment, at least one and preferably all of the extendable members of the SEC have an extendable fixation element disposed within a recess in the extendable member. In this embodiment, the implant is preferably fluid activated so the extendable members expand the SEC after implantation and be properly positioned between the adjacent vertebral bodies. Additionally, the fixation member is also extended by fluid pressure with or after expansion of the SEC. Preferably, the fluid expansion is by hydraulic fluid from a master cylinder or a syringe located remotely from the patient to enable controlled spinal correction in multiple dimensions and fixation of the SEC in a proper position. Individual cylinders or syringes may also be employed. Advantageously, the hydraulic fluid is a time-controlled curable polymer, such as methylmethacrylate, which has a viscosity and curing time that can be adjusted by the formulation of an appropriate added catalyst, as is well known. When the polymer cures, it hardens and locks the expanded expandable members and the expanded fixation element in position to provide the desired amount of anterior/posterior, medial/lateral, superior/inferior spinal correction immovably in place. Mechanical locking of the expandable members and/or the fixation elements may also be employed.

Once inserted between vertebral endplates, the implant advantageously can be expanded with a minimum of force exerted remotely through the hydraulic control lines. The expansion of the implant advantageously is about 20% to about 100% greater than the unexpanded height thereof, typically about 60%. Typical expansion is about 13 mm in the case of a 8 mm implant and about 16 mm in the case of a 10 mm implant.

Since the vertebral end plates are held together at one (the anterior) end by a ligament much like a clamshell, as the implant expands against the vertebral end plates, the amount of vertical expansion can be adjusted to create the desired anterior/posterior correction angle.

Left and right lateral correction of the spine is achieved by differential vertical expansion of the two or more extendable members of the implant. Each extendable member is preferably independently controlled by a master cylinder or syringe located ex vivo (away from the patient) and communicating hydraulically with the slave cylinders for moving the pistons and top plate vertically and laterally for correcting spinal deformities anteriorly or posteriorly, medial or lateral, thus available to provide spinal correction in three dimensions.

A minimally invasive downsized insertion tool both inserts the unexpanded SEC posteriorly and houses the hydraulic lines communicating between the master cylinder and the slave cylinder. The insertion tool also houses a line for communicating the liquid or slurry bone graft material to the slave cylinder and into the intervertebral space for subsequent fusion. Advantageously, the hydraulic lines are small size tubing to allow for high hydraulic pressure without danger of the lines bursting. The sizes of the slave cylinders and pistons can be varied to increase the mechanical advantage.

Due to the mechanical advantage provided by the hydraulic system, the SEC has minimized size and diameter in its unexpanded state that is smaller than the diameter of a prepared neuroforamen. The SEC thus can be inserted posteriorly and is engaged between the endplates of the adjacent vertebra to effectively distract the intervertebral area, restore space for neural elements, stabilize the motion segment and eliminate pathologic segmental motion. The SEC enhances spine arthrodesis by creating a rigid spine segment.

The SEC provides a significant advantage by enabling a comparatively large quantity of gone growth conductive or inductive agents to be contained within its interior communicating directly to adjacent bone. Importantly, this results in fixation forces greater than adjacent bone and soft tissue failure forces.

The hydraulic control system provides a minimally invasive procedure by enabling the surgeon to apply a controlling force away from the patient's body to expand and adjust the spinal implant in three dimensions. Preferably, the expansion is infinitely adjustable to provide a variety of height and lateral angles, and is not limited to incremental positions. The implant can be used to promote fusion, and/or to correct deformities such as scoliosis, kyphosis, and spondylolisthesis.

The clinical goals of the SEC and the method for its insertion provide a minimally invasive risk of trauma to nerve roots, reduce pain, improve function, and permit early mobilization of the patient after fusion surgery. The fixation elements maintain the implant in a desired position until healing (fusion or arthrodesis) occurs. At this point, the implant is incorporated inside bone and its role becomes quiescent. The present SEC provides more internal and external graft bone space exposure, easier and safer directed insertion, less risk of insertional damage to nerve roots and other tissue, and thus provide substantially improved immediate and long term results.

Thus, a key feature of the invention is that an essentially incompressible implant can be inserted posteriorly between vertebral pedicles in only a 1 cm working space. The implant then can be expanded to about 100% to about 200%, typically about 160%, of its original insertion size to provide a closely controlled full range of spinal correction in three dimensions. The one or more expandable fixation elements or spikes ensure that the implant remains in place after deployment. These and other advantages of the invention will become more apparent from the following detailed description and the accompanying exemplary drawings.

DETAILED DESCRIPTION

Figure 1:
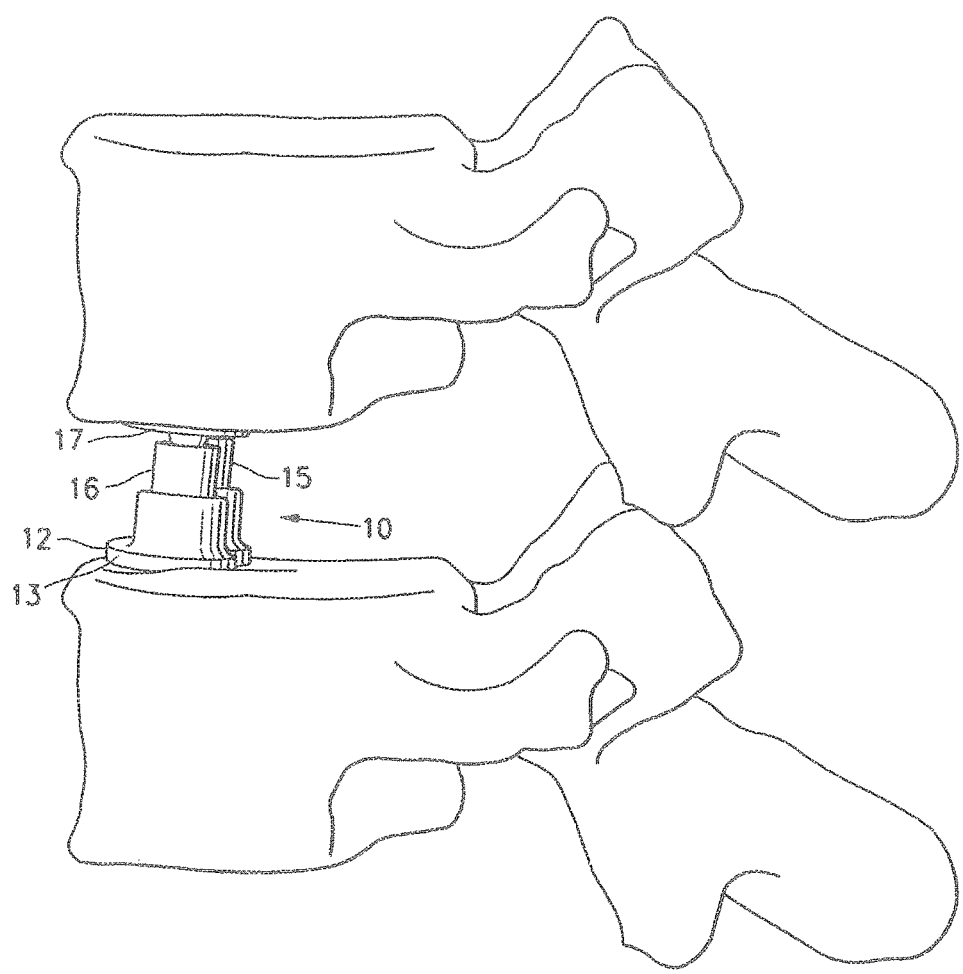
FIG. 1 depicts placement of an SEC embodying features of the invention between adjacent lumbar vertebrae.

FIG. 1 illustrates location of spinal implant or SEC 10 between adjacent lumbar vertebrae in an expanded configuration. A partial or complete discectomy is performed prior to the insertion of the spinal implant 10 in a conventional manner. The SEC 10 is introduced in its unexpanded state to enable it to be inserted posteriorly with minimal trauma to the patient and risk of injury to nerve roots. Once in place the SEC 10 can be expanded to provide both medial and lateral spinal correction. The SEC has an unexpanded height of about 5 to about 15 mm, typically about 10 mm and is expandable to at least 130% to about 180% of the unexpanded height. Typically the SEC is about 9 to about 15 mm, typically about 12 mm wide and about 25 to about 40 mm, typically about 28 mm long to facilitate posterior insertion and thereby minimize trauma to the patient and risk of injury to nerve roots.

Figure 2:
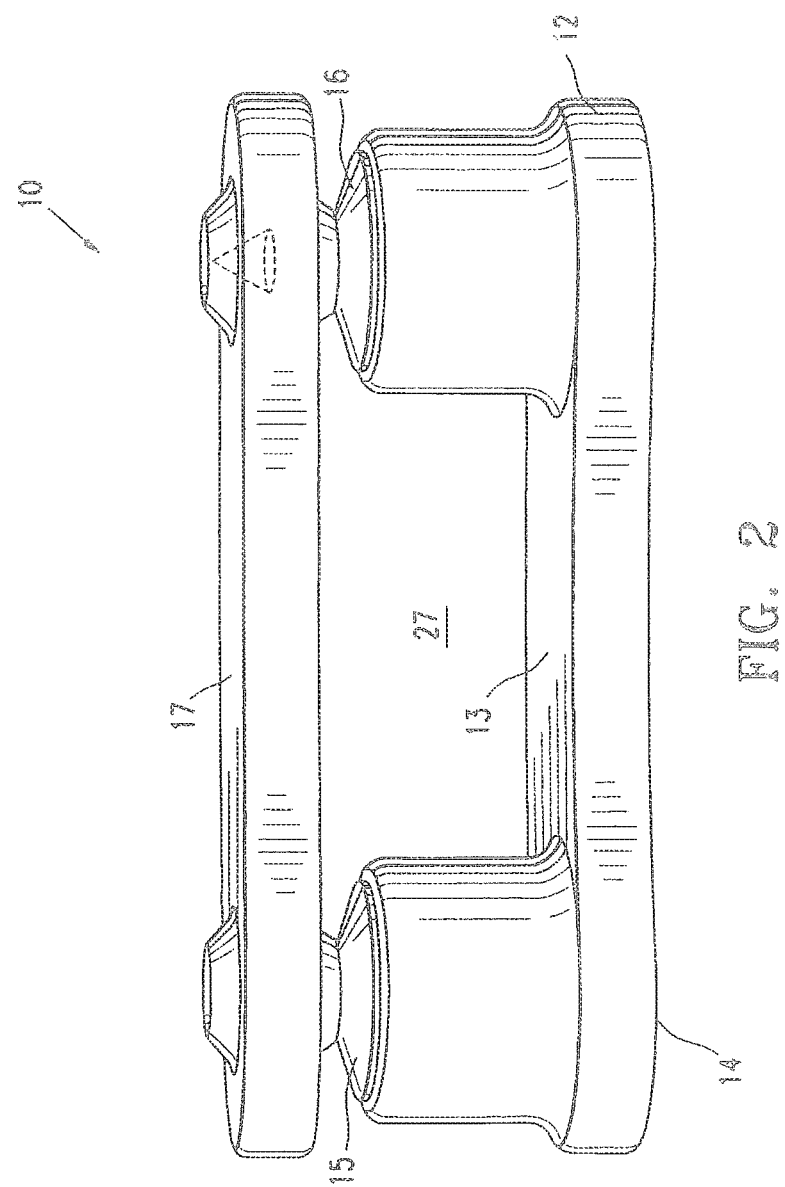
FIG. 2 is a front perspective view of the SEC shown in FIG. 1 in an unexpanded state prior to deployment.
Figure 3:
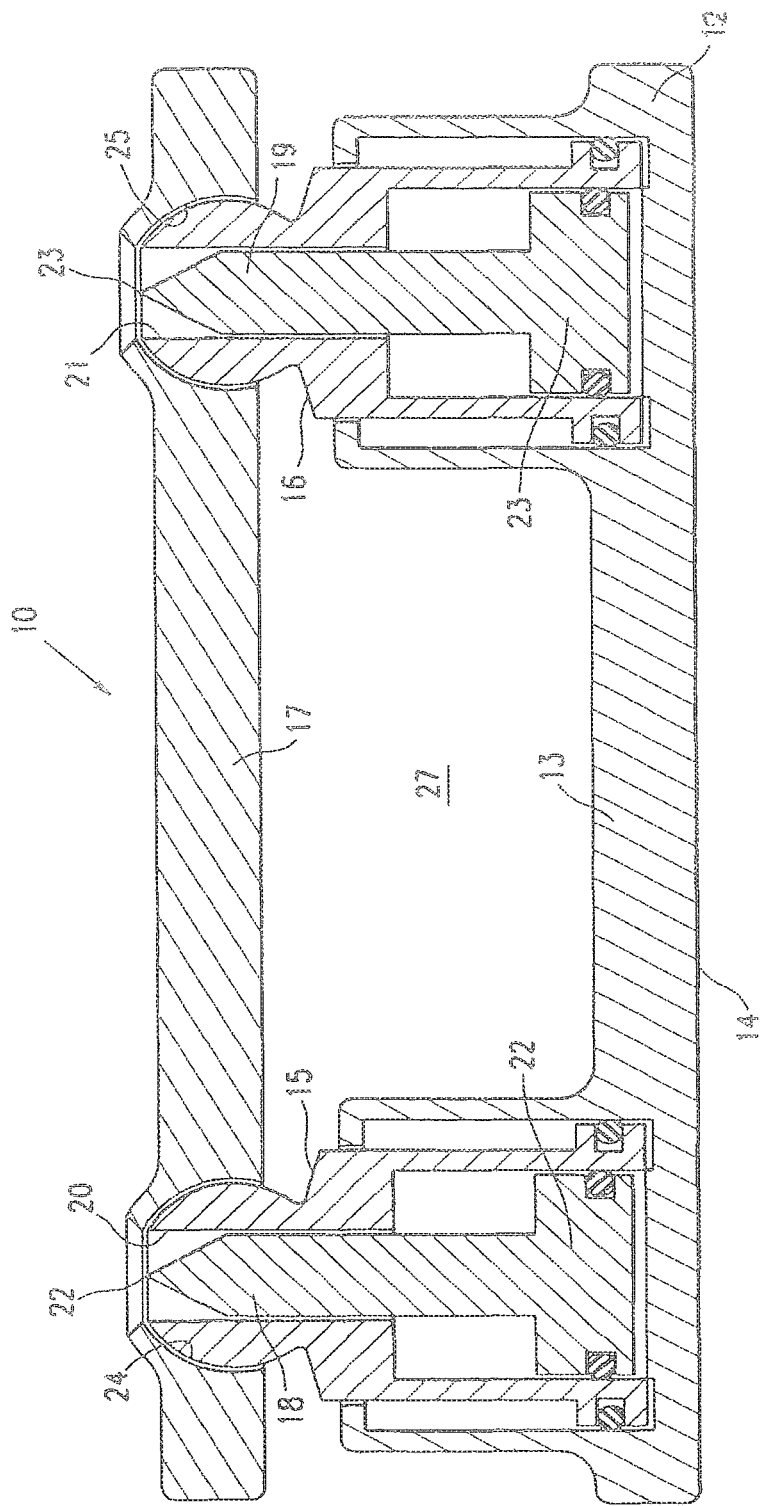
FIG. 3 is a sectional view of the SEC shown in FIG. 2.

FIG. 2 illustrate the SEC 10 in a closed or unexpanded configuration and FIG. 3 illustrates the SEC 10 in an expanded configuration in section or cutaway view to show the interior structure.

Figure 4:
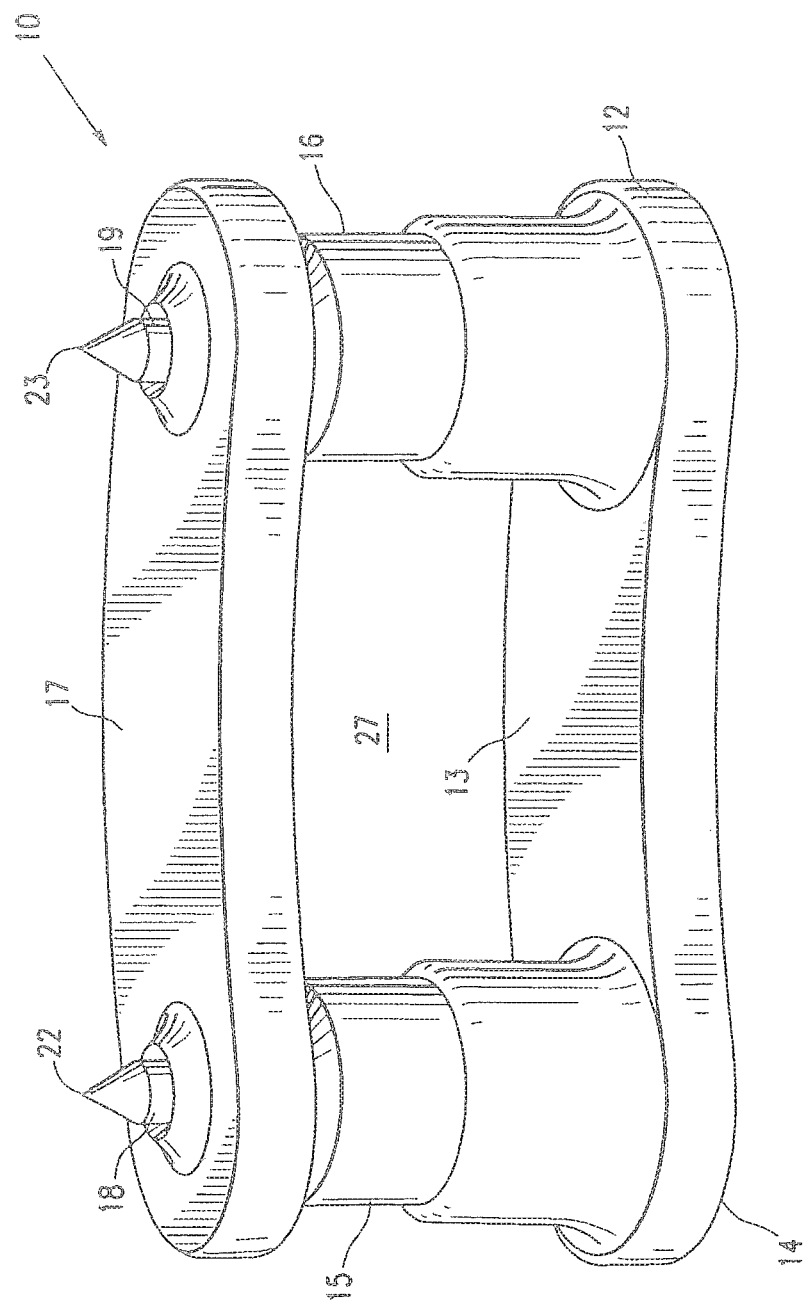
FIG. 4 is a front perspective view of the SEC of similar to that shown in FIG. 2 in an expanded configuration.

FIG. 4 illustrates the SEC 10 in an expanded configuration.

Figure 5:
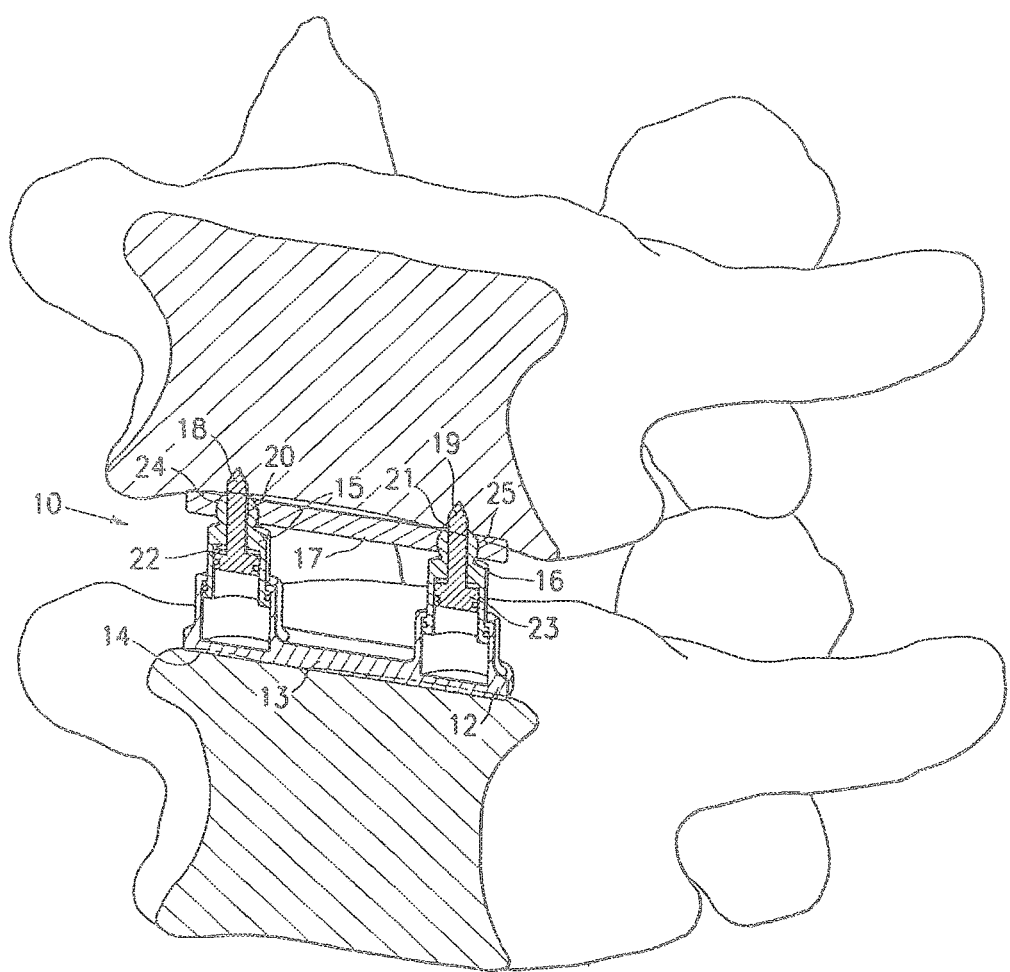
FIG. 5 is a partial sectional view of the expanded SEC shown in FIG. 4 in place adjacent to a vertebral body with the pointed ends of a fixation member penetrating the surface of the vertebral body.
Figure 6:
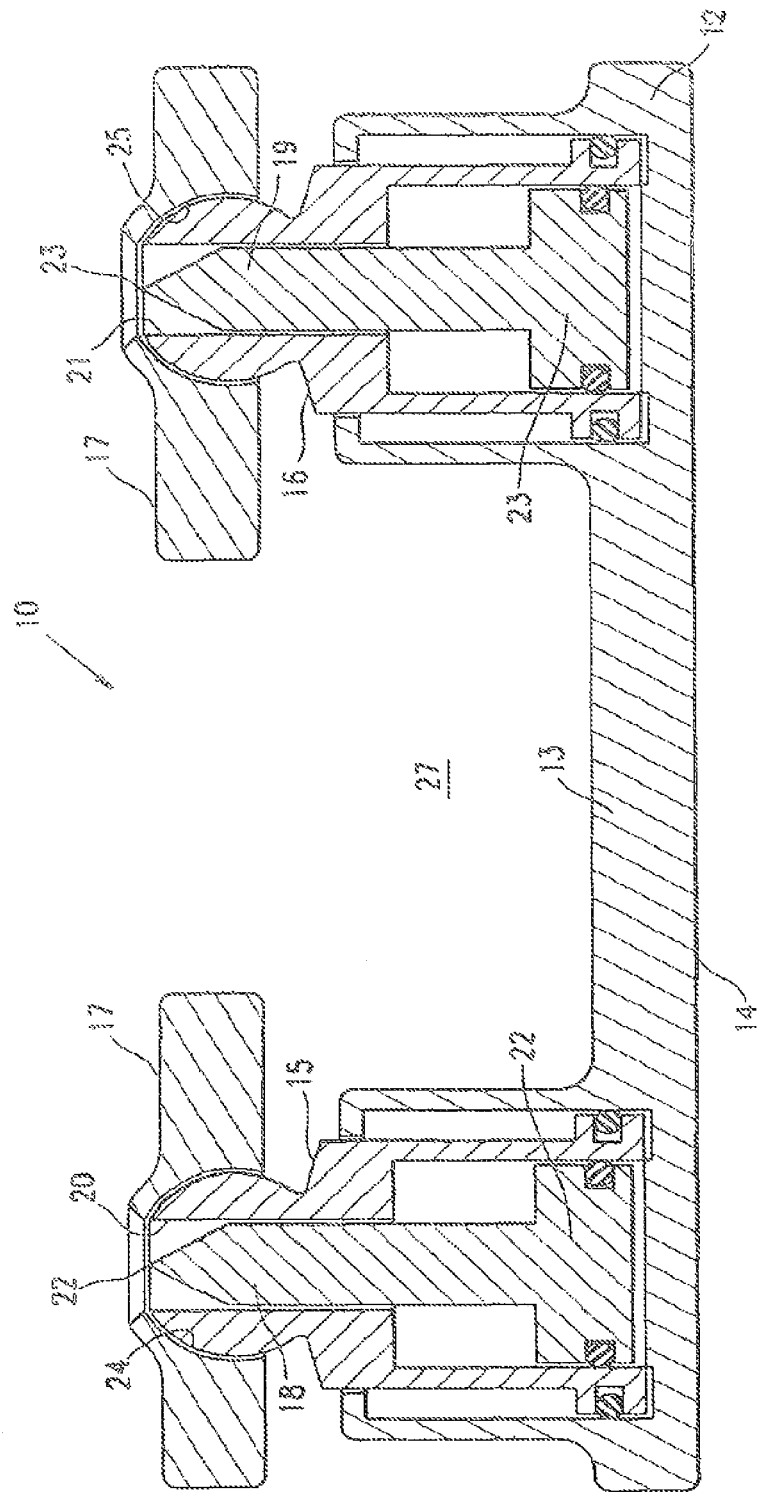
FIG. 6 is a sectional view of an alternative embodiment of the SEC.

As shown in these figures, the SEC 10 has a base 12 with a pressure applying end member or plate 13 having a surface 14 for engaging an end surface of an adjacent vertebral body. Extendable support members 15 and 16 cooperate with the base 12. A second end pressure applying member or plate 17 is coupled to the extendable support members 15 and 16 so that the plate 17 moves with the extension of extendable support members 15 and 16. The plate 17 may be fixed to only one of the extendable support member but also engageable with the other extendable support member. Each extendable support member may have a separate end plate fixed 17 thereto, as shown in FIG. 6. As shown in more detail in FIG. 3, the extendable support members 15 and 16 are provided with fixation elements or spikes 18 and 19 which are slidably disposed within the bores 20 and 21 of extendable support members 15 and 16. The spikes 18 and 19 are provided with enlarged bases 22 and 23 which provide a seal with the bores 20 and 21. The seal allows extension of the spikes 18 and 19 to be extended with the same pressurized hydraulic fluid (not shown) which extends the extendable support members 15 and 16. The spikes 18 and 19 are provided with pointed distal tips 22 and 23 which extend through passageways 24 and 25 provided in the end pressure plate 17 to ensure contact between the spikes and the adjacent vertebral body as shown in FIG. 5 so as to fix the SEC 10 within the space between the adjacent vertebral bodies. In FIG. 5, the SEC 10 is shown in the expanded configuration. The SEC 10 has a central cavity 27 for infusion of bone graft material into the intervertebral space when the SEC is fully expanded or during the expansion process.

Additional details of the SEC such as the attachment of hydraulic lines and lines for transmission of a slurry or liquid bone graft material, device and hydraulic fluid delivery accessories and the like can be found in co-pending application Ser. No. 11/535,432 filed on Sep. 26, 2006 and Ser. No. 11/692,800, filed on Mar. 28, 2007, which are incorporated herein by reference.

Since vertebral end plates are held together at one end by a ligament much like a clamshell, expansion of the device 10 against the end plates of adjacent vertebral bodies can be adjusted to create the desired anterior/posterior correction angle.

The hydraulic fluid used to expand the SEC 10 and to extend the spikes 18 and 19 may advantageously be a time-controlled curable polymer such as methylmethacrylate. The viscosity and curing time of such a polymer can be adjusted by the formulation with an appropriate added catalyst as is well known. Such catalysts are available from LOCTITE Corp., 1001 Trout Brook Crossing, Rocky Hill, Conn. 06067. When the polymer cures, it hardens and locks the extendable members 15 and 16 and the spikes 18 and 19 in a desired position to provide the desired amount of spinal correction determined by the physician. Other means may be employed to lock the extendable members and the spikes in a desired position. For example, spring actuated locking fingers may be provided in the bore of one or more of the pistons and one or more of the bores of the spikes which extend outwardly when the piston or spike pass their respective locations upon extension thereof.

It will be appreciated that the SEC, including its various components should be formed of biocompatible, substantially incompressible material such as titanium, and preferably type 6-4 titanium alloy or other suitable materials which will allow for long term deployment within a patient.

The extension of extendable members 15 and 16 are preferably individually controlled so that the physician is able to provide a controlled angle of the SEC corrective surface. While only two extendable members are described herein, the SEC 10 may be provided with three or more individually extendable members so that the physician can exercise three-dimensional control of the SEC extension.

The SEC 10 embodying features of the invention provides advantages that include correction of coronal plane deformity; introduction of interbody lordosis, early stabilization of the interbody space with rigidity that is greater than present spacer devices and the ability to fix the SEC within the intervertebral space. This early stability may improve post-operative pain, preclude the need for posterior implants including pedicle screws, and improve the rate of successful arthrodesis. Importantly, the SEC provides improvement of space available for the neural elements while improving lordosis. As infused osteoinductive/osteoconductive bone graft materials heal, the patient becomes well and the implant becomes inert and quiescent, embedded in bone, and no longer needed.

While the invention has been described in connection with what are presently considered to be the most practical and preferred embodiments, it is to be understood that the invention is not limited to the disclosed embodiments and alternatives as set forth above, but on the contrary is intended to cover various modifications and equivalent arrangements included within the scope of the following claims.

For example, the SEC 10 described herein is expanded by hydraulic fluid. Other expansion means may be employed. For example, a screw mechanism may be employed to expand the SEC and to extend one or more of the spikes into engagement with adjacent vertebral surfaces. Additionally, the spikes which help fix the SEC within the vertebral space are described herein as being extended with the extendable support members. However, the spikes may be slidably disposed in separate bores and independent expansion of the extendable support members.

Further, the SEC can be provided with load or pressure sensors that register differential pressure and pressure intensity exerted on the engaging surfaces of the SEC by the patient's vertebrae end plates to generate corrective signals, for example by control, that are used e.g. by the surgeon or by a computer controlled mechanism to realign the patient's spine. The invention may further include a system that makes these adjustments, responsive to sensor signals, in real time and on a continual basis, such that the shapes of the implant changes to realign the patient's spine or mechanism. Preferably, such system is contemplated for use in setting the positions of the pistons during installation of the implant.

Furthermore, the SEC needs not be rigidly locked into position but may be provided with yieldable material to provide some movement of the end surfaces of the SEC to accommodate spinal movement.

While particular forms of the invention have been illustrated and described herein, it will be apparent that various modifications and improvements can be made to the invention. Additional details of the spinal implant devices may be found in the patents and applications referenced herein. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.0 § 112(6) unless the following claims expressly use the terms "means for" or "step for" followed by a particular function without reference to a specific structure or a specific action. All patents and all patent applications referred to above are hereby incorporated by reference in their entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant for placement in a space between opposed first and second vertebral bodies, the implant comprising:
 a first surface for engaging the first vertebral body;
 a second surface for engaging the second vertebral body; and
 an extendable fixation element having a pointed distal tip, the extendable fixation element being extendable from a contracted configuration within the implant to an extended configuration in which the pointed distal tip extends beyond the second surface to engage the second vertebral body and fix the implant within the space between the first and second vertebral bodies;
 wherein the implant is configured to be operable by a user to selectively drive the first surface away from the second surface, and wherein the extendable fixation element is extendable independently of the expansion of the implant.

2. The implant of claim 1, wherein the implant is adapted to be expanded by a pressurized fluid.

3. The implant of claim 1, wherein the extendable fixation element is extendable through an opening in the second surface at a plurality of angles relative to the second surface.

4. The implant of claim 1, wherein the extendable fixation element comprises a first extendable fixation element and a second extendable fixation element.

5. The implant of claim 4, wherein the first and second extendable fixation elements are extendable independently of one another.

6. The implant of claim 1, wherein the implant is expanded by extending a first extendable support member and a second extendable support member.

7. The implant of claim 6, wherein the first extendable support member comprises a first support member received with a first cylinder and slidable along a longitudinal dimension of the first cylinder, and wherein the second extendable support member comprises a second support member received within a second cylinder and slidable along a longitudinal dimension of the second cylinder.

8. The implant of claim 6, wherein the first and second extendable support members are extendable independently of one another.

9. The implant of claim 8, wherein the first surface is positioned on a first end plate adapted to engage the first vertebral body, wherein the second surface is positioned on a second end plate and a third end plate adapted to engage the second vertebral body, wherein the first extendable support member is coupled to the first end plate and the second end plate, the first extendable support member being extendable so as to move the second end plate away from the first end plate, wherein the second extendable support member is coupled to the first end plate and the third end plate, the second extendable support member being extendable so as to move the third end plate away from the first end plate, and wherein the second and third end plates are separate from one another such that the independent extension of the first and second extendable support members independently moves the respective second and third end plates.

10. The implant of claim 9, wherein the second and third end plates are adapted to independently change angles with respect to the first end plate.

11. The implant of claim 10, wherein the first extendable support member is pivotably coupled to the second end plate at a first pivot point that is fixed with respect to the second end plate, such that the second end plate is constrained to pivot about the first pivot point, and wherein the second extendable support member is pivotably coupled to the third end plate at a second pivot point that is fixed with respect to the third end plate, such that the third end plate is constrained to pivot about the second pivot point.

12. The implant of claim 6, wherein the first and second extendable support members are laterally spaced apart from one another along a dimension of the first surface of the implant.

13. The implant of claim 12, wherein a central cavity is defined between the laterally spaced apart first and second support members, the central cavity configured to receive bone graft material for infusion from the central cavity into the space between the first and second vertebral bodies.

* * * * *